United States Patent [19]

Yamazaki et al.

[11] Patent Number: 5,496,549
[45] Date of Patent: Mar. 5, 1996

[54] BISPECIFIC MONOCLONAL ANTIBODIES, THROMBOLYTIC AGENT AND METHOD OF CELL LYSIS

[75] Inventors: Hiroh Yamazaki, Tokyo; Kenjiro Tanoue, Ibaraki; Susumu Iwasa, Kyoto; Tomofumi Kurokawa, Hyogo, all of Japan

[73] Assignees: Takeda Chemical Industries, Ltd., Osaka; Tokyo Metropolitan Institute of Medical Science, Tokyo, both of Japan

[21] Appl. No.: 350,497

[22] Filed: Dec. 6, 1994

Related U.S. Application Data

[63] Continuation of Ser. No. 673,323, Mar. 22, 1991, abandoned.

[30] Foreign Application Priority Data

Apr. 2, 1990 [JP] Japan ................................ 2-088985
Jul. 3, 1990 [JP] Japan ................................ 2-177121

[51] Int. Cl.$^6$ .................. A61K 51/00; A61K 51/10; A61K 38/49; C07K 16/38
[52] U.S. Cl. .................. 424/158.1; 424/134.1; 424/136.1; 424/145.1; 424/182.1; 424/94.63; 530/387.3; 530/388.1; 530/388.25; 530/391.7
[58] Field of Search ............... 530/387.3, 388.1, 530/388.25, 391.7; 424/136.1, 134.1, 145.1, 158.1, 94.63

[56] References Cited

U.S. PATENT DOCUMENTS

| | | |
|---|---|---|
| 4,474,893 | 10/1984 | Reading . |
| 4,714,681 | 12/1987 | Reading . |
| 4,734,279 | 3/1988 | Stephan et al. .................. 424/85 |
| 4,889,922 | 12/1989 | Schaumann et al. ............. 530/413 |

FOREIGN PATENT DOCUMENTS

| | | |
|---|---|---|
| 363712 | 4/1990 | European Pat. Off. . |
| 83/03679 | 10/1983 | WIPO . |
| 87/06240 | 10/1987 | WIPO . |

OTHER PUBLICATIONS

Kurokawa, T. et al., Thrombosis Res, Supp X:83–89, Aug. 27, 1989.
Haber, E. et al., Science, 243:51–56, Jan. 6, 1989.
Milstein, C. et al., Immun. Today, 5(10):299–304, 1984.
Scheefers–Borchel, V. et al., PNAS, 82:7091–7095, Oct. 1985.
Kurokawa, T., et al., Biotechnology, 7:1163–1167, Nov. 1989.
Palabrica, et al., Proc. Natl. Acad. Sci. USA 86:1036–1040 (1989).
Bode, et al., The Journal of Biological Chemistry, 262(2):944–948 (1989).
McEver, Thrombosis and Haemostasis, 62:3 (1989).
Akamatu, et al., Thrombosis and Haemostasis, 62:250 (1989).

*Primary Examiner*—Margaret Parr
*Assistant Examiner*—Susan A. Loring
*Attorney, Agent, or Firm*—David G. Conlin; David S. Resnick

[57] ABSTRACT

Disclosed are a bispecific hybrid MoAb having specificity for both an activated platelet and a substance having thrombolytic activity, and a thrombolytic agent comprising the above bispecific MoAb and a substance having thrombolytic activity immunologically bound thereto, whereby efficient, rapid thrombolysis is possible.

13 Claims, 5 Drawing Sheets

BISPECIFIC MONOCLONAL ANTIBODIES, THROMBOLYTIC AGENT AND METHOD OF CELL LYSIS

This is a continuation of application Ser. No. 07/673,323 filed on Mar. 22, 1991, now abandoned.

FIELD OF THE INVENTION

The present invention relates to a bispecific hybrid monoclonal antibody, and more particularly to a hybrid monoclonal antibody (hereinafter occasionally referred to as hybrid MoAb) specific for both an activated platelet and a substance having thrombolytic activity.

In another aspect the present invention is further directed to a thrombolytic agent comprising the above-mentioned hybrid MoAb and a substance having thrombolytic activity immunologically bound thereto.

BACKGROUND OF THE INVENTION

Thrombolytic therapeutics have formerly been used for treatment of thrombotic diseases such as cardiac infarction, arterial embolism and cerebral infarction. At first, streptokinase (hereinafter occasionally referred to as SK) and urokinase (hereinafter occasionally referred to as UK) were clinically employed as useful thrombolytic agents. In particular, UK was relatively frequently employed because of its high fibrinolysis activity. However, UK has the disadvantage that its selectivity for fibrin is low, and that it also acts on fibrinogen resulting in the tendency to cause bleeding in patients who it is given to.

Then, considering such a disadvantage, tissue plasminogen activator (hereinafter occasionally referred to as TPA) and prourokinase (hereinafter occasionally referred to as ProUK) appeared as the second-generation thrombolytic agents. These agents had higher fibrin selectivity than that of UK, and were therefore expected to reduce the bleeding side effect observed in UK. Accordingly, many studies focused on these agents. In particular, mass production of theses agents by recombinant technology has recently begun. In addition, their clinical applications have been extensive (*European Cooperative Study Group for Recombinant Tissue-Type Plasminogen Activator: The Lancet,* Vol.1, 842 (1985)).

However, these clinical applications have revealed that TPA and related agents have also problems. Namely, (1) the half-life of TPA is very short (2 to 3 minutes), so that it is necessary for thrombolysis that TPA is given in large amounts for a long period of time, and (2) a reduction in bleeding tendency can not always be expected in such therapeutics in which TPA is given in large amounts.

As a result of these problems, more effective thrombolytic agents were studied and developed. These included the preparation of modified TPA and the hybrid protein of TPA and UK or ProUK. As to modified TPA, a TPA mutein partially lacking the sugar chain structure which is considered to be the cause of a reduction in half-life is prepared by genetic engineering techniques to avoid the capture with sugar chain receptors such as hepatocytes, thereby intending to improve the kinetics in blood. For the hybrid protein of UK and TPA, the strong thrombolytic activity of UK is used in combination with the fibrin affinity of TPA, thereby aiming at reducing the dosage. These thrombolytic agents can be expected to decrease the bleeding tendency slightly compared to those known in the art. However, significant improvement depends on future studies and developments.

Then, as the third-generation thrombolytic agents, protein complexes utilizing antibody targeting appeared. Namely, thrombolytic agents that decompose fibrin alone, without decomposing fibrinogen were developed by chemically binding antibodies substantially unreactive to fibrinogen and having high affinity for fibrinogen alone to UK (C. Bode et al., *Science* 229, 765 (1985)) or TPA (M. S. Runge et al., *Proc. Natl. Acad. Sci. USA* 84, 7659 (1987)). It has been reported that such antibody targeted thrombolytic agents exhibited the effect 3 to 100 times higher than that of single active ingredient preparations of UK or TPA in each of in vitro and in vivo experiments. In each of these protein complexes, however, an antibody is chemically bound to a thrombolytic enzyme. Therefore, these complexes have the disadvantages that (1) the chemical binding operation is accompanied by a reduction in antibody activity and in enzyme activity, (2) it is difficult to obtain the protein complexes having an antibody-enzyme ratio of 1:1 in good yields, and (3) as a result of protein denaturation, metabolism in the patients who are given the complexes is accelerated or immune response is induced.

Then, a thrombolytic agent specific for fibrin and having no side effects was developed by preparing a bispecific MoAb which could be bound at one binding site thereof to fibrin and at the other binding site thereof to a thrombolytic active substance, and immunologically binding the thrombolytic active substance to this antibody to prepare an immune complex having a bispecific MoAb-thrombolytic active substance ratio of 1:1, which was not accompanied by a reduction in antibody activity and in thrombolytic activity (see Japanese Patent Unexamined Publication No. 2-500321/1990, European Patent Unexamined Publication No. 363712/1990).

In the above-mentioned bispecific MoAb-thrombolytic active substance immune complex, the reactivity to fibrinogen is almost negligible. Hence, the immune complex specifically, efficiently acts on lysis of thrombi formed in vivo, which contain fibrin as a main constituent. However, almost all of the thrombi formed in vivo are accompanied by platelets, and some of them are formed containing a large amount of platelets (in a platelet-rich state).

SUMMARY OF THE INVENTION

To enhance thrombolytic activity of the anti-fibrin-antithrombolytic active substance bispecific MoAb, and to lyse the platelet-rich thrombi efficiently, the present inventors succeeded in developing a thrombolytic agent specific and effective for thrombi by preparing a bispecific MoAb which specifically reacts at one binding site thereof with an activated platelet and at the other binding site thereof with a substance having thrombolytic activity, and further, immunologically binding the substance having thrombolytic activity to this antibody in a ratio of 1:1, and completed the present invention by conducting more extensive investigations.

The present invention provides a bispecific hybrid MoAb having specificity for both an activated platelet and a substance having thrombolytic activity.

The present invention further provides a thrombolytic agent comprising the above-mentioned bispecific MoAb and a substance having thrombolytic activity immunologically bound thereto.

DESCRIPTION OF THE PREFERRED EMBODIMENTS

Figure 1:
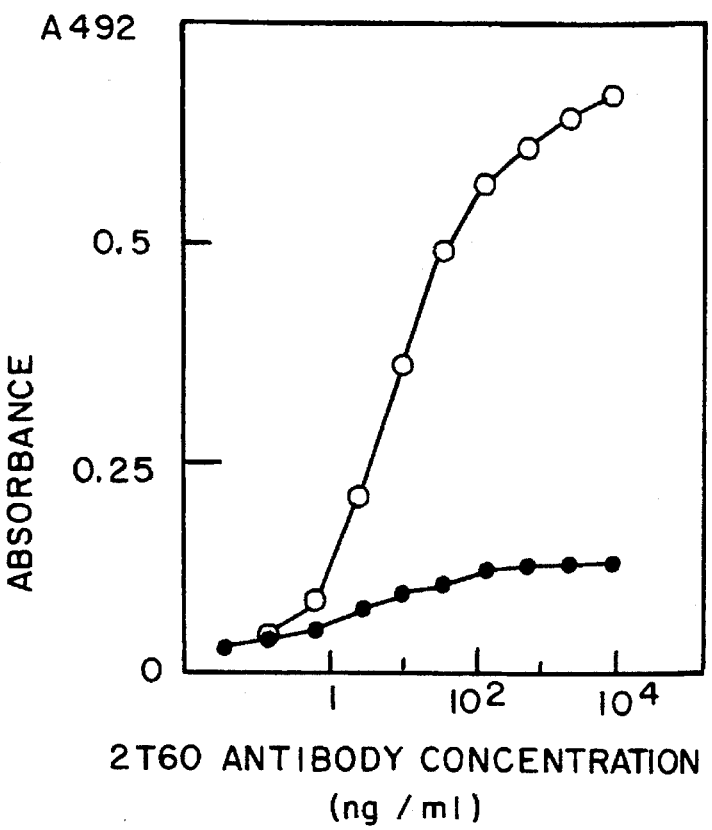
FIG. 1 is a graph showing the results of the reactivity of anti-activated platelet antibody 2T60 to activated human platelets (o) and resting platelets (•) described in Example 1, the reactivity being measured by the enzyme immunoassay (hereinafter occasionally referred to as EIA) described in Reference Example 1 (see Example 1)

In the present invention, the activated platelets include platelets responsible for blood coagulation. Examples of such platelets include platelets activated with thrombin, collagen and adenosine 5'-diphosphate (ADP), (activation with thrombin is preferable).

The monoclonal antibodies specific for the activated platelets (anti-activated platelet MoAbs) include MoAbs which specifically bind to the activated platelets, but do not substantially bind to resting platelets. Such MoAbs include, for example, MoAbs which specifically recognize membrane proteins of platelets appearing together with the activation with thrombin and similar substances (T. M. Palabrica et al., Proc. Natl. Acad. Sci. USA 86, 1036 (1989); R. P. McEver, Thromb. Haemostasis 62, 3 (1989); and N. Akamatsu et al., Thromb. Haemostasis 62, 250 (1989)).

In the preparation of anti-activated platelet MoAb-producing hybridomas, any hybridomas may be used as long as they produce MoAbs which are specific for the activated platelets and do not substantially bind to the resting platelets. For example, such activated platelet specific MoAbs are prepared by using as immunogens, platelets (preferably human platelets) activated with thrombin (C. L. Berman et al., J. Clin. Invest. 78, 130 (1986); and N. Akamatsu et al., Thromb. Haemostasis 62, 250 (1989)). Any platelets may be used as long as they are mammalian. Preferred examples thereof include human platelets.

Animals such as rabbits, rats, mice and guinea pigs are immunized with the activated platelets to obtain antibody-producing cells. Next, these antibody-producing cells recovered from the immunized animals, such as spleen cells and lymphatic node cells, are fused with myeloma cells. The antibody-producing cells which do not substantially react with the resting platelets and specifically bind to the activated platelets are screened from the resulting hybridomas, whereby the desired anti-activated platelet MoAb-producing hybridoma cells can be obtained.

As the substances having thrombolytic activity (hereinafter occasionally referred to as thrombolytic active substance), any substances may be used as long as they are proteins having thrombolytic activity or substances promoting thrombolyticv activity. Examples thereof include proteases, precursors thereof and thrombolysis-promoting substances (for example, TPA, UK, ProUK, trypsin, plasmin, protein C and Protein S). In particular, proteases are preferably used, and more preferably, TPA and UK are used. TPA may be single-chain or two-chain types, and UK may also be single-chain or two-chain types (E. Haber et al., Science 243, 51 (1989)). Furthermore, low molecular weight UK and ProUK may be used.

In the preparation of anti-thrombolytic substance MoAb-producing hybridomas, animals are immunized with the above-mentioned proteins according to methods known in the art, and the resulting antibody-producing cells are fused with myeloma cells and myeloma-like cells. In particular, in the preparation of anti-UK antibody-producing hybridomas, it is convenient to use antibody-producing cells obtained by immunizing animals with low molecular weight UK. The immunization of the animals and the fusion of the resulting antibody-producing cells with the myeloma cells to obtain the antibody-producing hybridoma cells may be carried out similarly with the preparation of the anti-activated platelet antibody-producing hybridoma cells.

Examples of the animals for immunization include rabbits, rats, mice and guinea pigs. When the MoAbs are prepared, mice are preferably used. The inoculation is performed according to a standard method. For examples, when the antibody specific for the activated platelets is prepared, $10^8$ to $10^{10}$, preferably $0.5 \times 10^9$ to $2 \times 10^9$ washed human platelets each time suspended in physiological saline, Hepes buffer or phosphate buffered saline (hereinafter occasionally referred to as PBS) are activated with thrombin, and then inoculated into mice intraperitoneally, 3 to 8 times every 10 to 14 days. When the antibody specific for the thrombolytic active substances is prepared, 1 to 100 μg each time, preferably 10 to 25 μg each time of the thrombolytic active substance emulsified with an equal volume (0.1 ml) of physiological saline and Freund's complete adjuvant is inoculated into mice subcutaneously in the back or the abdomen or intraperitoneally, 3 to 6 times every 2 to 3 weeks.

Individuals having a high antibody titer are selected from these immunized animals such as mice, and their spleens or lymphatic nodes are recovered therefrom 3 to 5 days after the final immunization. Then, antibody-producing cells contained therein are fused with myeloma cells. The fusing operation may be conducted according to methods known in the art. Fusogens include polyethylene glycol (hereinafter occasionally referred to as PEG) and Sendai virus, PEG is preferably used. The myeloma cells include NS-1, P3U1 and Sp2/0. In particular, NS-1 and P3U1 are preferably used. For example, the preferable ratio of the number of the spleen cells to that of the myeloma cells is 1:1 to 10:1. It is preferred that PEG having a molecular weight of 1,000 to 9,000 is added thereto in a concentration of 10 to 80%, and that the resulting mixture is incubated at 20° to 37° C., and preferably at 30° to 37° C., for 3 to 10 minutes.

Various methods can be used for screening of the anti-activated platelet MoAb-producing hybridoma cells. For example, a microplate to which thrombin-activated platelets are bound and fixed with 1% formalin is used as a solid phase antigen. The hybridoma culture supernatant is added thereto, and the antibody titer of the culture supernatant is determined by an enzyme immunoassay in which the anti-activated platelet antibody bound to the microplate is detected by a second enzyme-labeled antibody. Then, hybridoma cells having large differences between bindings to the resting platelets and to the activated platelets are selected. For example, hybridoma cells having positive antibody activity which is selected in HAT (hypoxanthine, aminopterin and thymidine) medium are immediately subjected to cloning, which can be conducted by the limiting dilution method. The antibody titer of the cloned hybridoma culture supernatant is determined by the above-mentioned method and hybridoma cells which stably produce antibody having a high titer are selected. Thus, the desired monoclonal anti-activated platelet specific antibody-producing hybridoma cells can be obtained.

Examples of the anti-activated platelet MoAb-producing hybridoma cells prepared according to the above methods include mouse hybridoma 2T60 shown in Example 1 described below.

The screening of the hybridoma cells which produce the MoAb to the substance having thrombolytic activity (anti-thrombolytic active substance MoAb) can be carried out by an EIA using a microplate on which the substance is adsorbed. The cloning is also conducted according to the known method described above. Thus, the desired anti-thrombolytic active substance MoAb-producing hybridoma cells can be obtained.

Examples of the anti-TPA MoAb-producing hybridoma cells prepared by the above methods include mouse hybridoma TPA 1- 41, TPA 1-70 and TPA 2-14 described in Reference Example 9 below. Examples of the anti-UK MoAb-producing hybridoma cells include mouse hybridoma UK1-3 and UK1-87 described in Reference Example 11 below, and mouse hybridoma UK1-6 described in Reference Example 12.

The bispecific hybrid MoAbs of the present invention are prepared by several methods. One method is a chemical binding method. In this method, the MoAb specific for the activated platelets is covalently bound to the MoAb to the substance having thrombolytic activity. In another method, two kinds of hybridoma cells each producing the anti-activated platelet MoAb and the anti-thrombolytic active substance MoAb are fused with each other to prepare hybrid hybridoma cells (such as tetraoma cells), thereby preparing the desired bispecific antibody. As means for obtaining the antibodies of a constant high grade in large amounts in good yields, the latter hybrid hybridoma method is preferably used.

To bind two kinds of MoAbs to each other, substituent groups contained in antibody molecules such as amino groups, carboxyl groups, hydroxyl groups and sulfhydryl groups can be utilized. For example, the following methods are used:

(1) A reactive amino group contained in one antibody is condensed by dehydration with a reactive carboxyl group contained in another antibody in an aqueous solvent by using a water-soluble carbodiimide reagent (for example, 1-ethyl- 3-(3-dimethylaminopropyl)-carbodiimide, 1-cyclohexyl-3-(2-morpholinoethyl)-carbodiimide or p-toluene sulfonate).

(2) A reactive amino group contained in one antibody is reacted with an active ester of N-hydroxysuccinimide (for example, an ester of p-maleimidomethylcyclohexane-1-carboxyl-N-hydroxysuccimide or an ester of N-(ε-maleimidocaproyloxy)succinimide) to maleimidate the amino group, and then the resulting maleimidated group is bound by a thioether bond to (i) another antibody reduced with dithiothreitol (DTT), (ii) another antibody into which a sulfhydryl group is introduced by using N-succimidyl-3-(2-pyridyldithio)propionate (SPDP), or (iii) a sulfhydryl group of a Fab' fraction obtained by reduction of another antibody treated with pepsin.

(3) Both reactive amino groups of two kinds of antibodies are bound to each other by using a dialdehyde reagent such as succindialdehyde or glutaraldehyde.

(4) Two kinds of antibodies are reduced with DTT, or sulfhydryl groups are introduced into them by using SPDP, followed by reoxidization to prepare a heterodimer.

(5) Two kinds of antibodies are both treated with pepsin, and then reduced to obtain an Fab' fraction, followed by reoxidization to prepare an Fab' heterodimer. There are reports that desired heterodimeric bispecific antibodies are efficiently prepared with impairing the activity of two kinds of antibodies as little as possible by combining the above-mentioned methods variously (M. J. Glennie et al., *J. Immunol.* 139, 2367 (1987); and T. Kitagawa, *Organic Synthetic Chemistry* 42, 283 (1984)). These methods can be employed to prepare the bispecific hybrid MoAbs of the present invention.

After the binding reaction described above has been completed, the bispecific antibody-bound products can be purified and isolated by gel filtration chromatography using Sephadex G100 or G200 (pharmacia), Sepharose 6B or 4B(Pharmacia), Ultrogel AcA44 or 34(LKD), Sephacryl S200 (Pharmacia), or the like. Selective isolation is also possible by combination with affinity chromatography using an antigen-bound column.

There are several methods to prepare the hybrid hybridoma cells which can be used to produce the bispecific hybrid monoclonal antibodies of the present invention (for example, H. Shinmoto et al., *Proteins, Nucleic Acids, Enzymes* 33, 217 (1988)), and any methods may be used. Examples thereof include the following methods:

(1) The above HAT-resistant anti-thrombolytic active substance MoAb-producing hybridoma cells are conditioned stepwise in a culture solution containing 5-bromodeoxyuridine (hereinafter occasionally referred to as BrdU), whereby the thymidine kinase-deficient strain is cloned to turn it HAT-sensitive. Similarly, the HAT-resistant anti-activated platelet specific MoAb-producing hybridoma cells are made 8-azaguanine-resistant (8-azaguanine is hereinafter occasionally referred to as 8-AZG), and the hypoxanthine-guanine-phosphoribosyl transferase- deficient strain is cloned to turn it HAT-sensitive. Then, both are fused with each other according to a standard method. The resulting tetraoma cells are selected in HAT medium, and then the tetraoma cells are cloned which secrete hybrid MoAbs having affinity for both of the activated platelets and the substance having thrombolytic activity.

(2) The anti-activated platelet specific MoAb-producing hybridoma cells are labeled with fluorescein isothiocyanate (hereinafter occasionally referred to as FITC), and the anti-thrombolytic active substance MoAb-producing hybridoma cells is labeled with tetramethylrhodamine isothiocyanate (hereinafter occasionally referred to as TRITC). Then, both are fused with each other by a standard method. The resulting cell suspension is subjected to a fluorescein activated cell sorter (hereinafter occasionally referred to as FACS) to select and clone tetraoma cells having both green fluorescence of FITC and red fluorescence of TRITC. It is also possible to use the markers of both parent strains in reverse, thereby selecting and cloning the tetraoma cells.

For cell fusion in this manipulation, fusogens such as Sendai virus and PEG, and electrical stimulation are used. PEG is preferably used. One example thereof will hereinafter be described. However, the scope of the present invention is not limited thereto. Namely, PEG having a molecular weight of about 1,000 to 9,000 is used in a concentration of about 10 to 80%. The reaction time is about 0.5 to 30 minutes. For example, PEG 6,000 is allowed to contact with cells in a concentration of about 35 to 55% at 37° C. for about 4 to 10 minutes to perform the fusion efficiently.

Selection of the polydoma cells (such as tetraoma cells) can be carried out in the above HAT medium. The polydoma cells are conditioned with drugs such as 8-AZG, 6-thioguanine (6-TG) and 5-BrdU to obtain the respective drug-resistant strains. Further, various selection media are used by the introduction of a new marker into fused cells. Examples of such media include neomycin-added media and hygromycin B-added media (B. Sugden et al., *Mol. Cell. Biol.*, 5, 410 (1985)).

Further, a method may be used in which the hybridoma cells each labeled with different fluorescent dyes are fused with each other and the doubly-fluorescienated hybrid hybridoma cells are sorted using FACS (L. Karawajew et al., *J. Immunol. Methods* 96, 265 (1987)).

The hybrid antibody-producing polydoma cells can be screened by various methods. For example, the following methods and their modified methods can be suitably used in combination:

(1) A combination of EIAs for screening the above-mentioned anti-activated platelet specific MoAb-producing hybridoma cells and the anti-thrombolytic active substance MoAb-producing hybridoma cells;

(2) An EIA for detecting a bispecific hybrid antibody by adding a culture supernatant to be tested to an activated platelet-bound microplate, and then adding an HRP-labeled substance having thrombolytic activity thereto;

(3) When an anti-thrombolytic active substance antibody belonging to a subclass different from that of an anti-activated platelet specific antibody is used, an EIA for detecting a bispecific antibody by adding a culture supernatant to be tested to an activated platelet-bound microplate, and then adding the HRP-labeled anti-mouse IgG subclass specific antibody thereto.

Polydoma cells having positive antibody activity are immediately subjected to cloning, which can be conducted using a limiting dilution method. The antibody titer of the cloned polydoma culture supernatant is determined by the above-mentioned method, and polydoma cells which stably produce an antibody having a high titer are selected. Thus, the desired monoclonal hybrid antibody-producing polydoma cells can be obtained.

Usually, the above-mentioned polydoma cells of the present invention can be cultivated in liquid media or in peritoneal cavities of animals (for example, in peritoneal cavities of mammals such as mice) by methods known in the art. The antibodies in culture solutions or ascites fluid can be purified using biochemical techniques known in the art in combination. For example, a cell culture solution or ascites fluid is centrifuged to obtain a supernatant. The supernatant is removed and subjected to salt precipitation (usually ammonium sulfate or sodium sulfate is used). The resulting protein precipitate is dissolved in an appropriate solution. After dialysis, the solution is submitted to column chromatography such as ion-exchange column, gel filtration column, protein A column or hydroxyapatite column chromatography. Thus, the desired antibody can be separated and purified. By such separation and purification procedures, for example, about 1 to 5 mg of the hybrid MoAb having a purity of more than 80% by protein weight ratio can be obtained from 1 liter of the culture supernatant. Further, 3 to 10 mg of a similar antibody can be obtained from 20 ml of ascites fluid.

The bispecific hybrid MoAbs obtained as described above are homogeneous as proteins, and when treated with proteases such as pepsin, $F(ab')_2$ fragments having affinity for the activated platelets and the substance having thrombolytic activity can be obtained. These fragments can be used for a purpose similar to that of the hybrid MoAbs of the present invention.

The hybrid MoAb-producing polydoma cells prepared by the methods described above include, for example, mouse hybridoma (tetraoma) UP3-175 shown in Example 2 described below.

As the polydoma cells producing the hybrid MoAbs of the present invention, the tetraoma cells of the anti-activated platelet MoAb-producing hybridoma cells and the anti-thrombolytic active substance MoAb-producing hybridoma cells were exemplified. However, trioma cells of hybridoma cells producing one MoAb and cells producing the other MoAb, or hybridoma cells obtained by immortalizing cells which produce each MoAb with Epstein-Barr virus, followed by cell fusion can also be used for a purpose similar to that of the above-mentioned tetraoma cells, as long as they produce the hybrid MoAbs of the present invention.

In particular, in a method in which spleen cells of the animals immunized with the thrombolytic active substance are fused with the anti-activated platelet specific MoAb-producing hybridoma cells, trioma cells having proliferation potency are limited to ones derived from the hybridoma cells which can produce the anti-activated platelet MoAbs. Hence, the desired bispecific antibody-producing trioma cells can be selected by using only methods for assaying antibody activity to the thrombolytic active substances. Various bispecific antibody-producing trioma cells can be efficiently obtained by such methods.

When these polydoma cells produce mouse IgG hybrid MoAb, a mouse-human chimera antibody can be prepared by obtaining a DNA sequence coding for a variable region or a hypervariable region containing an antigen recognition site of the bispecific hybrid MoAb, ligating the DNA sequence to a gene coding for a constant region of human IgG using gene manipulation technology (Z. Steplewski et al., *Proc. Natl. Acad. Sci. USA* 85, 4852 (1988)). When given to humans, such a chimera antibody is favorably used because of its little antigenicity.

In thrombolytic therapeutics using selective thrombolytic protein complexes prepared from the bispecific hybrid MoAbs of the present invention, or the substances having thrombolytic activity and the bispecific hybrid MoAbs, several methods are used. Examples thereof include the following methods:

(1) A hybrid MoAb of the present invention is preliminarily given to patients with thrombotic diseases, and a substance having thrombolytic activity such as TPA or UK is given, after a sufficient time to ligate the MoAb to thrombi formed in the bodies of the patients has elapsed.

(2) The hybrid MoAb and the substance having thrombolytic activity are simultaneously given to patients with thrombotic diseases.

(3) The hybrid MoAb is preliminarily reacted with the substance having thrombolytic activity, and the unreacted thrombolytic substance is removed. Then, the resulting selective thrombolytic protein complex is given to patients with thrombotic diseases.

The thrombolytic agents, the hybrid MoAbs and the substances having thrombolytic activity of the present invention are formed into preparations such as injections, as themselves alone or as mixtures of them with pharmaceutically acceptable carriers, excipients, diluents and the like, after filtration and sterilization procedures with membrane filters if necessary, and are given to mammals such as mice, rats, cats, dogs, pigs, cattle, monkeys and humans. They can be used for treatment of thrombotic obstructive diseases such as cardiac infarction, peripheral arterial or venous obstruction, retinal arterial or venous obstruction, cerebral infarction and pulmonary embolism.

The dosage of the thrombolytic agents of the present invention varies depending on the subject disease, symptom, route of administration and the like. For example, when the thrombolytic agent is intravenously given to adult human patients with cardiac infarction, the hybrid MoAb is used in an amount of about 0.02 to 1 mg/kg daily, preferably about 0.04 to 0.4 mg/kg daily, and the substance having thrombolytic activity is used in an amount of about 0.01 to 0.5 mg/kg daily, preferably about 0.02 to 0.2 mg/kg daily, for TPA, in an amount of about 0.01 to 0.5 mg/kg, preferably about 0.02 to 0.2 mg/kg, for UK, and in an amount of about 0.01 to 1 mg/kg, preferably about 0.02 to 0.5 mg/kg, for ProUK.

The thrombi can be lysed and removed selectively and efficiently even if the thrombi are platelet-rich by using the hybrid MoAb of the present invention which specifically binds to a target thrombotic site and does not substantially bind to resting platelets, and the substance having thrombolytic activity, according to the methods described above. Further, the thrombi can be lysed and removed more efficiently and rapidly by using the bispecific hybrid MoAb of the present invention in combination with the anti-fibrin-anti-thrombolytic active substance bispecific MoAb and giving simultaneously with the thrombolytic active substance.

The present invention will hereinafter be described in detail with the following Reference Examples and Examples. It is understood of course that these Reference Examples and Examples are not intended to limit the scope of the invention.

The animal cells used in Reference Examples and Examples are deposited in the deposition institutes as shown in the following table:

| Animal cell | IFO (IFO No.) | FRI (FERM NO.) |
| --- | --- | --- |
| Mouse hybridoma F1B1-11 | 50174 (Sep. 21, 1988) | BP-2081 (Nov. 4, 1988) |
| Mouse hybridoma 2T60 | 50211 (Sep. 27, 1989) | BP-2623 (Nov. 4, 1989) |
| Mouse hybridoma TPA1-41 | 50178 (Sep. 21, 1988) | BP-2085 (Nov. 4, 1988) |
| Mouse hybridoma TPA1-70 | 50179 (Sep. 21, 1988) | BP-2086 (Nov. 4, 1988) |
| Mouse hybridoma TPA2-14 | 50194 (Jul. 14, 1989) | BP-2519 (Jul. 18 1989) |
| Mouse hybridoma UK1-3 | 50176 (Sep. 21, 1988) | BP-2083 (Nov. 4 1988) |
| Mouse hybridoma UK1-87 | 50177 (Sep. 21, 1988) | BP-2084 (Nov. 4 1988) |
| Mouse hybridoma UK1-6 | 50208 (Aug. 9, 1989) | BP-2548 (Aug. 11, 1989) |
| Mouse hybrid hybridoma UP3-175 | 50224 (Feb. 21, 1990) | BP-2845 (Mar. 30, 1990) |
| Mouse hybrid hybridoma UP4-33 | 50251 (Jul. 3, 1990) | BP-3018 (Jul. 13, 1990) |
| Mouse hybrid hybridoma FU1-74 | 50185 (Mar. 13, 1989) | BP-2344 (Mar. 14, 1989) |

IFO: The Institute for Fermentation, Osaka, 17–65 Juso-hommachi 2-chome, Yodogawa-ku, Osaka 532 Japan
FRI: The Fermentation Research Institute, the Agency of Industrial Science and Technology, the Ministry of International Trade and Industry, 1–3, Higashi 1-chome, Tsukuba-shi Ibaraki-ken 305, Japan Reference Example 1

EIA for Measuring Anti-Platelet Antibody
(1) Preparation of Fixed Platelets

Platelet-rich plasma was obtained by centrifugation from fresh human blood collected by using sodium citrate, and washed with Tyrode-Hepes buffer (pH 6.5) containing an ADP-hydrolyzing enzyme. The washed platelets were seeded in a microplate in an amount of $2\times10^7$ platelets/well, and activated with thrombin (0.2 units/ml), followed by centrifugation. Then, after fixing with 2% formalin, the plate was blocked with PBS containing 5% bovine serum albumin (hereinafter occasionally referred to as BSA) to prepare an activated platelet plate. A resting platelet plate was prepared in the same manner as above with the exception that the thrombin activating procedure was omitted.
(2) EIA Procedure To the platelet plate was added 100 μl/well of a hybridoma culture supernatant, followed by reaction at room temperature for 3 hours. The plate was washed with PBS containing 0.05% Tween 20 (PBS-TW), and horseradish peroxidase (HRP)-labeled rabbit anti-mouse IgG antibody was added thereto, and further reacted at room temperature for 2 hours.

After washing, 0.1M citrate buffer containing o-phenylenediamine and $H_2O_2$ was added to each well, and enzyme reaction was conducted at room temperature. The reaction was terminated with 1N sulfuric acid, and then the amount of color-developed dye was determined at 492 nm with Multiscan (Flow Laboratory).

Reference Example 2

EIA for Measuring Anti-TPA Antibody

A 5 μg/ml TPA solution was added to a 96-well microplate in an amount of 100 μl/well and allowed to stand overnight at 4° C. Then, 150 μl/well of PBS containing 2% casein and 0.01% thimerosal was added thereto to prepare a sensitized plate. The above solution was removed from the microplate and the microplate was washed with PBS-TW. Then, 100 μl/well of a test hybridoma culture supernatant was added thereto and reacted at room temperature for 2 hours. Thereafter, enzyme reaction was conducted according to the method described in Reference Example 1 and the antibody titer was assayed.

Reference Example 3

EIA for Measuring Anti-UK Antibody

A UK-sensitized plate was prepared in the same manner as with Reference Example 2 with the exception that TPA was substituted for UK, and the anti-UK antibody titer was similarly assayed.

Reference Example 4

EIA for Measuring Anti-Low Molecular Weight UK Antibody

A low molecular weight UK-sensitized plate was prepared in the same manner as with Reference Example 2 with the exception that TPA was substituted for low molecular weight UK (two chain low molecular weight UK, sold by JCR) and the anti-low molecular weight UK antibody titer was similarly assayed.

Reference Example 5

EIA for Measuring Anti-Activated Platelet-Anti-UK Hybrid Antibody

A test hybridoma culture supernatant was added to the activated platelet-sensitized plate prepared in Reference Example 1 and reacted at room temperature for 2 hours. After washing with PBS-TW, biotin-labeled UK was added thereto and further reacted at room temperature for 2 hours. Then, an avidin-HRP complex was added thereto, followed by reaction at room temperature for 1 hour. Thereafter, the activity of HRP bound to the solid phase was assayed by the method described in Reference Example 1.

Reference Example 6

EIA for Measuring Anti-Activated Platelet-Anti-TPA Hybrid Antibody

The bispecific antibody titer was assayed in the same manner as with Reference Example 5 with the exception that biotin-labeled UK was substituted for biotin-labeled TPA.

Reference Example 7

Neutralization Test of Fibrinolysis Reaction

A diluted solution of a test hybridoma culture supernatant was added to a TPA solution (final concentration: 20 ng/ml) or a UK solution (final concentration: 25 ng/ml), and reacted at 37° C. for 1 hour. Then, the reaction mixture was poured into each well of a fibrin agarose plate in an amount of 5 μl. After standing at 37° C. for 2 to 6 hours, the diameter of the halo of fibrinolysis was measured to determine the neutralization activity of a MoAb contained in the hybridoma culture supernatant to the enzyme activity of TPA or UK.

Reference Example 8

Neutralization Test of UK Enzyme Activity

A test antibody solution was added to a UK solution (final concentration: 1.7 μg/ml) and reacted at room temperature for 30 minutes, followed by addition of peptide synthesis substrate S-2444 (1 mM, pyroglutamyl glycyl arginyl p-nitroanilide, Kabi). After further reaction at 37° C. for 15 minutes, released p-nitroanilide (absorbance at 405 nm) was measured.

Reference Example 9

Preparation of Mouse Anti-TPA Monoclonal Antibody-Producing hybridomas
(1) Immunization To 200 μg of commercial single-chain TPA in 1 ml of physiological saline, an equal volume of Freund's complete adjuvant was added and fully emulsified. The emulsion was then given to the BALB/c mice (females, 20 μg/0.2 ml/mouse) intraperitoneally and subcutaneously in their backs, and booster immunization was carried out at intervals of 2 to 3 weeks. After the booster immunization was conducted 3 times, a TPA antigen solution (50 μg/0.1 ml of physiological saline/mouse) was intravenously given to the individual which showed the highest serum antibody titer after 10 days.
(2) Cell Fusion The spleen was taken out of the mouse 3 days after the final immunization, and a spleen cell suspension containing about $10^8$ cells was prepared by a standard method. Then, 2×10 mouse myeloma cells (P3U1) were added thereto, and cell fusion was conducted by using PEG 6000 according to the method of Kohler and Milstein (*Nature* 256, 495 (1975)).

After completion of the fusion, the cell mixture was suspended in HAT medium containing hypoxanthine, aminopterin and thymidine, and cultivated for 10 days. Then, immediately after selection of parent cells was completed, HT medium was substituted for HAT medium from which aminopterin was eliminated, and the cultivation was continued.
(3) Selection and Cloning of Hybridomas The antibody titer of the hybridoma culture supernatants was determined by the EIA of Reference Example 2 using a microplate in which TPA was adsorbed on a solid phase. After 10 to 20 days from the fusion, hybridoma cells and an antibody which could specifically bind to TPA were observed. The hybridoma cells having particularly high binding activity were cloned by the limiting dilution method.

Similarly, the cloned hybridoma culture supernatants were screened by the EIA described in Reference Example 2, and three kinds of anti-TPA MoAb-producing mouse hybridoma cells having high binding activity to TPA, mouse hybridomas TPA1-41, 1-70 and 2-14, were obtained. Their immunoglobulin class and subclass were examined by the Ouchterlony test. They were found to belong to $IgG_{2b}$, $IgG_1$ and $IgG_1$, respectively.
(4) Preparation of Monoclonal Antibodies Into a BALB/C mouse preliminarily given 0.5 ml of mineral oil intraperitoneally, $5\times10^6$ MoAb-producing hybridoma cells were inoculated intraperitoneally. After about 10 to 15 days, the pool of ascites fluid was observed.

Antibodies were purified by a standard method. Namely, the antibodies were fractionated by 45–50% saturated ammonium sulfate, and then subjected to DEAE-cellulose column chromatography and protein A column chromatography. Consequently, mouse anti-TPA monoclonal antibodies TPA1-41, TPA1-70 and TPA2-14 were obtained from mouse hybridomas TPA1-41, TPA1-70 and TPA2-14, respectively.

Reference Example 10

Neutralization Activity of Anti-TPA Monoclonal Antibodies to TPA Fibrinolysis Activity The anti-TPA MoAbs prepared in Reference Example 9-(4) were subjected to the neutralization test of fibrinolysis reaction using the fibrin agarose plate described in Reference Example 7 to assay the neutralization activity to TPA.

As a result, antibodies TPA1-14 and TPA1-70 exhibited weak neutralization activity and strong neutralization activity, respectively. However, antibody TPA2-14 showed no neutralization activity at all.

Reference Example 11

Preparation of Mouse Anti-UK Monoclonal Antibody-Producing Hybridomas
(1) Immunization
The mice were immunized in the same manner as with Reference Example 9-(1) with the exception that TPA is substituted for UK (Nippon Seiyaku).
(2) Cell Fusion
Cell fusion was carried out according to the method described in Reference Example 9-(2).
(3) Selection and Cloning of Hybridomas
Hybridoma cells were screened by the EIA of Reference Example 3 using the UK-bound microplate, and anti-UK MoAb-producing hybridoma cells were obtained in the same manner as with Reference Example 9-(3). Of these, mouse hybridomas UK1-3 and UK1-87 were obtained as anti-UK MoAb-producing hybridoma cells having binding specificity to UK without impairing its fibrinolysis activity. The immunoglobulin class and subclass of mouse anti-UK MoAbs UK1-3 and UK1-87 produced from the resulting hybridoma cells were found to be $IgG_1$ and $IgG_{2b}$, respectively, by the Ouchterlony test.

Reference Example 12

Preparation of Mouse Anti-Low Molecular Weight UK Monoclonal Antibody-Producing Hybridoma
(1) Immunization
The mice were immunized in the same manner as with Reference Example 9-(1) with the exception that TPA was substituted for commercial two-chain low molecular weight UK (sold by JCR).
(2) Cell Fusion
Cell fusion was carried out according to the method described in Reference Example 9-(2).
(3) Selection and Cloning of Hybridoma
Hybridoma cells were screened by the EIA of Reference Example 4 using the low molecular weight UK-bound microplate, and anti-low molecular weight UK MoAb-producing hybridoma cells were obtained in the same manner as with Reference Example 9-(3). Of these, mouse hybridoma UK1-6 was obtained as anti-low molecular weight UK MoAb-producing hybridoma having binding specificity to UK without impairing its fibrinolysis activity. The immunoglobulin class and subclass of mouse anti-UK MoAb UK1-6 produced from the resulting hybridoma were found to be $IgG_1$ (κ chain) by the Ouchterlony test.

Reference Example 13

Purification of Anti-UK Monoclonal Antibodies
Anti-UK monoclonal antibody-producing hybridomas UK1-3, UK1-87 and UK1-6 obtained in Reference Examples 11 and 12 were inoculated to form ascites fluid in the same manner as with Reference Example 9-(4). Further, the resulting ascites fluid was purified by salt precipitation and column chromatography to obtain mouse anti-UK monoclonal antibodies UK1-3, UK1-87 and UK1-6.

Reference Example 14

Neutralization Activity of Anti-UK Monoclonal Antibodies
Mouse anti-UK monoclonal antibodies UK1-3, UK1-87 and UK1-6 obtained in Reference Example 13 were subjected to the neutralization test of UK enzyme activity of Reference Example 8 using synthetic peptide substrate S-2444. All of the mouse anti-UK monoclonal antibodies did not impair the UK antibody activity.

Reference Example 15

EIA for anti-fibrin antibody measurement
To a 96-well microplate was dispensed a 1 mg/ml human fibrin monomer solution in a phosphate buffer solution (PBS, pH 7.3) containing 3.3M urea and 0.01% EDTA at 50 μl per well. After leaving this microplate at 4° C. overnight, 150 μl of PBS containing 2% casein and 0.01% thimerosal was added to prepare a sensitized plate. Then, a 10 mg/ml human fibrinogen solution in PBS containing 100 units/ml heparin and 3 mM phenylmethyl sulfonyl fluoride was mixed with an equal amount of the subject hybridoma culture supernatant. After reaction at room temperature for 30 minutes, 100 μl of the mixture was added to the above fibrin-sensitized plate, followed by reaction at room temperature for 2 hours. After thoroughly washing the plate with 0.05% PBS-TW, a HRP labeled rabbit anti-mouse-IgG antibody was added, followed by reaction at room temperature for 2 hours. Thereafter, enzyme reaction was carried out by the method of Reference Example 1 and antibody titer was determined.

Reference Example 16

EIA for measuring anti-fibrin-anti-UK hybrid antibody (2)
To a UK-sensitized plate as prepared in Reference Example 3 was added the subject solution containing the hybrid antibody, followed by reaction at room temperature for 2 hours. After plate washing with PBS-TW, the human fibrin β-chain N-terminal peptide (1-11)-BSA complex described in Reference Example 17-(1), labeled with biotin, was added, followed by reaction at room temperature for 2 hours. An avidin-HRP complex was then added, followed by reaction at room temperature for 1 hour; the activity of HRP bound to the solid phase was determined by the method of Reference Example 1.

Reference Example 17

Preparation of hybridomas which produce mouse anti-human-fibrin monoclonal antibody
(1) Preparation of immunogen
To an aqueous solution of 12 mg/2 ml bovine serum albumin (BSA), previously maleimidated with GMBS (maleimido groups were introduced at 13 moles per mole BSA), was added 3.3 mg of a human fibrin β-chain N-terminal peptide (1-11)-Cys prepared by the known solid phase synthesis method using a peptide synthesizer (Model 430A, Applied System Co.), followed by reaction at 30° C. for 1 hour to yield a human fibrin β-chain N-terminal peptide (1-11)-BSA complex. After 3 times of dialysis with physiological saline solution (3 liter×3), this complex was stored frozen and then used as immunogen.
(2) Immunization To a 1 mg/ml peptide-BSA complex solution in physiological saline solution was added an equal amount of Freund's complete adjuvant, followed by subcutaneous immunization of mice (o, n=10:0.1 mg/0.2 ml/mouse) at the back and abdomen. Additional immunization was conducted by inoculating the immunogen in combination with an equal amount of Freund's incomplete adjuvant 5 times at intervals of 2 to 3 weeks.

(3) Cell fusion

At 3 days following the final immunization, spleens were excised and a splenocyte suspension was prepared by a standard method (about $10^8$ cells). After addition of $2 \times 10^7$ mouse myeloma cells (P3U1), cell fusion was conducted in accordance with the method of Kohler and Milstein (*Nature*, 256, 495(1975)) using PEG 6000.

After completion of the fusion, the cell mixture was suspended in HAT medium, which contains hypoxanthine, aminopterin and thymidine, followed by cultivation for 10 days. Immediately after completion of the selection of parent cells, the HAT medium was replaced with HT medium, which lacks aminopterin, followed by further cultivation.

(4) Selection and cloning of hybridomas

The antibody titer of the hybridoma culture supernatant was determined by the EIA procedure described in Reference Example 1, which uses a human fibrin monomer adsorbed microplate as the solid phase. At 10 to 20 days following the fusion, hybridomas appeared and an antibody which specifically bound to human fibrin was detected. The hybridomas found to have especially strong avidity were subjected to cloning by a limiting dilution method.

The culture supernatant of cloned hybridomas was subjected to screening by EIA; hybridomas with strong avidity to human fibrin were selected.

As a result, mouse hybridomas FIB1-11 was obtained, which produced an MoAb which specifically binds to fibrin in the presence of high concentrations of fibrinogen. Antibody FIB 1-11 produced by the hybridoma was identified as $IgG_1$ in immunoglobulin class and subclass by the Ouchterlony method.

Reference Example 18

Production of hybrid monoclonal antibody possessing anti-UK-anti-human-fibrin bispecificity (1) Cell fusion In accordance with the method described in Example 2-(1), the hybridoma FIB1-11 obtained in Reference Example 17, which produces anti-human-fibrin antibody, and the hybridoma UK1-3 obtained in Reference Example 11, which produces anti-UK antibody, were each subjected to fluorescent staining with FITC and TRITC, followed by cell fusion using PEG 6000. The cell mixture was applied to FACS; double-stained cells were selected and cultivated.

(2) Selection and cloning of hybrid hybridomas

The culture supernatants from wells in which cell proliferation occurred at 1 to 2 weeks following the fusion were each subjected to the EIA procedure described in Reference Examples 3, 15 and 16 to determine their antibody activity.

The well which exhibited the maximum hybrid antibody activity was subjected to cloning by a limiting dilution method to obtain the desired bispecific-antibody-producing mouse hybridoma FU1-74.

(3) Purification of hybrid antibody

Ascites fluid was collected in accordance with the method described in Example 2-(3), followed by salting-out with ammonium sulfate and immuno-affinity chromatographhy using a fibrin-coupled column and a UK-coupled column; 14 mg of FU 1-74, the anti-UK-anti-human-fibrin bispecific antibody of the present invention, was obtained from about 20 ml of ascites fluid.

EXAMPLE 1

Preparation of Mouse Anti-Activated Platelet Antibody-Producing Hybridoma (1) Immunization Washed platelets were obtained by centrifugation from fresh human blood collected by using sodium citrate.

To about $10^9$ platelets, 0.1 unit/ml of thrombin was added and incubated at 37° C. for 5 minutes, followed by intraperitoneal injection to the BALB/c mice. Immunization was carried out 6 to 8 times at intervals of 2 weeks.

(2) Cell Fusion

Cell fusion was carried out in the same manner as with Reference Example 9-(2) with the exception that mouse myeloma cell P3U1 is substituted for NS-1.

(3) Selection and Cloning of Hybridoma

Hybridoma cells were screened by the EIA of Reference Example 1 using the platelet-bound microplate, and anti-activated platelet MoAb-producing hybridoma was obtained in the same manner as with Reference Example 9-(3). As a result, MoAb-producing hybridoma 2T60 specifically bindable to activated human platelets and activated rabbit platelets was obtained.

(4) Preparation of Monoclonal Antibody

According to the method described in Reference Example 9-(4), mouse anti-activated platelet MoAb 2T60 was obtained from mouse ascites fluid. The immunoglobulin class and subclass of antibody 2T60 were found to be $IgG_1$ (κ chain) by the Ouchterlony test.

Figure 2:
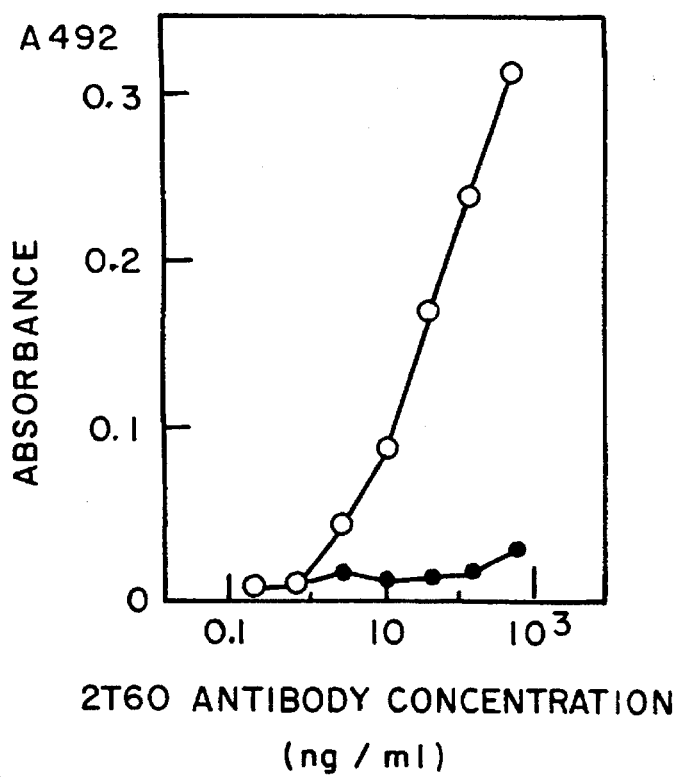
FIG. 2 is a graph showing the results of the reactivity of anti-activated platelet antibody 2T60 to activated rabbit platelets (o) and resting platelets (•) described in Example 1, the reactivity being measured by the EIA described in Reference Example 1 (see Example 1)

Anti-activated platelet MoAb 2T60 described above was measured by the EIA of Reference Example 1 using the human platelet-bound microplate. The results thereof are shown in FIG. 1. Further, anti-activated platelet MoAb 2T60 was measured by the same method as that described in Reference Example 1 with the exception that the human platelets were substituted for rabbit platelets. The results thereof are shown in FIG. 2. FIGS. 1 and 2 reveal that antibody 2T60 shows reactivity only to the activated platelets of humans and rabbits, and does not substantially show reactivity to the resting platelets.

EXAMPLE 2

Preparation of Hybrid Monoclonal Antibody Having Anti-UK-Anti-Activated Platelet Bispecificity (1)

(1) Cell Fusion

Anti-activated platelet MoAb-producing hybridoma 2T60 obtained in Example 1 and anti-low molecular weight UK MoAb-producing hybridoma UK1-6 obtained in Reference Example 12 were incubated in Iscove-Ham F12 mixed medium containing 0.5 µg/ml FITC and that containing 1.5 µg/ml TRITC, respectively, at 37° C. for 30 minutes, followed by fluorescent staining. Then, an LSM solution (sold by Wako Pure Chemical Industries) was added thereto to remove dead cells, and thereafter both hybridoma cells were mixed with each other in a ratio of 1:1. Using PEG 6000, cell fusion was conducted by the method described in Reference Example 9-(2).

After incubation at 37° C. for 2 hours, 25,000 cells were separately taken from cells stained double with fluorescein and rhodamine by subjecting the cells to an FACS. Then, the above-mentioned double-stained cells were seeded in a concentration of 10 cells/well in a 96-well microplate in which 5×10⁵ cells/well of mouse thymocytes had been seeded, and cultivated.

(2) Selection and Cloning of Trioma

For wells which were positive in the EIA described in Reference Example 5, cloning was performed by the limiting dilution method. As a result, mouse hybrid hybridoma UP3-175 was obtained which showed high hybrid antibody activity.

(3) Purification of Hybrid Antibody

Into 6 BALB/c mice preliminarily given 0.5 ml of mineral oil intraperitoneally, 5×10⁶ cells/mouse of mouse hybrid hybridoma UP3-175 were inoculated intraperitoneally. After about 10 to 20 days, the pool of ascites fluid was observed. The ascites fluid was collected, and subjected to salt precipitation using 45–50% saturated ammonium sulfate to obtain an IgG fraction.

Then, the fraction was subjected to a UK-bound column equilibrated with 20 mM PBS (pH 8.0). A protein fraction which was eluted with 0.05M glycine-hydrochloric acid buffer (pH 2.3) was collected, and then applied to high performance liquid chromatography using a hydroxyapatite column to obtain mouse anti-UK-anti-activated platelet bispecific MoAb UP3-175.

Figure 3:
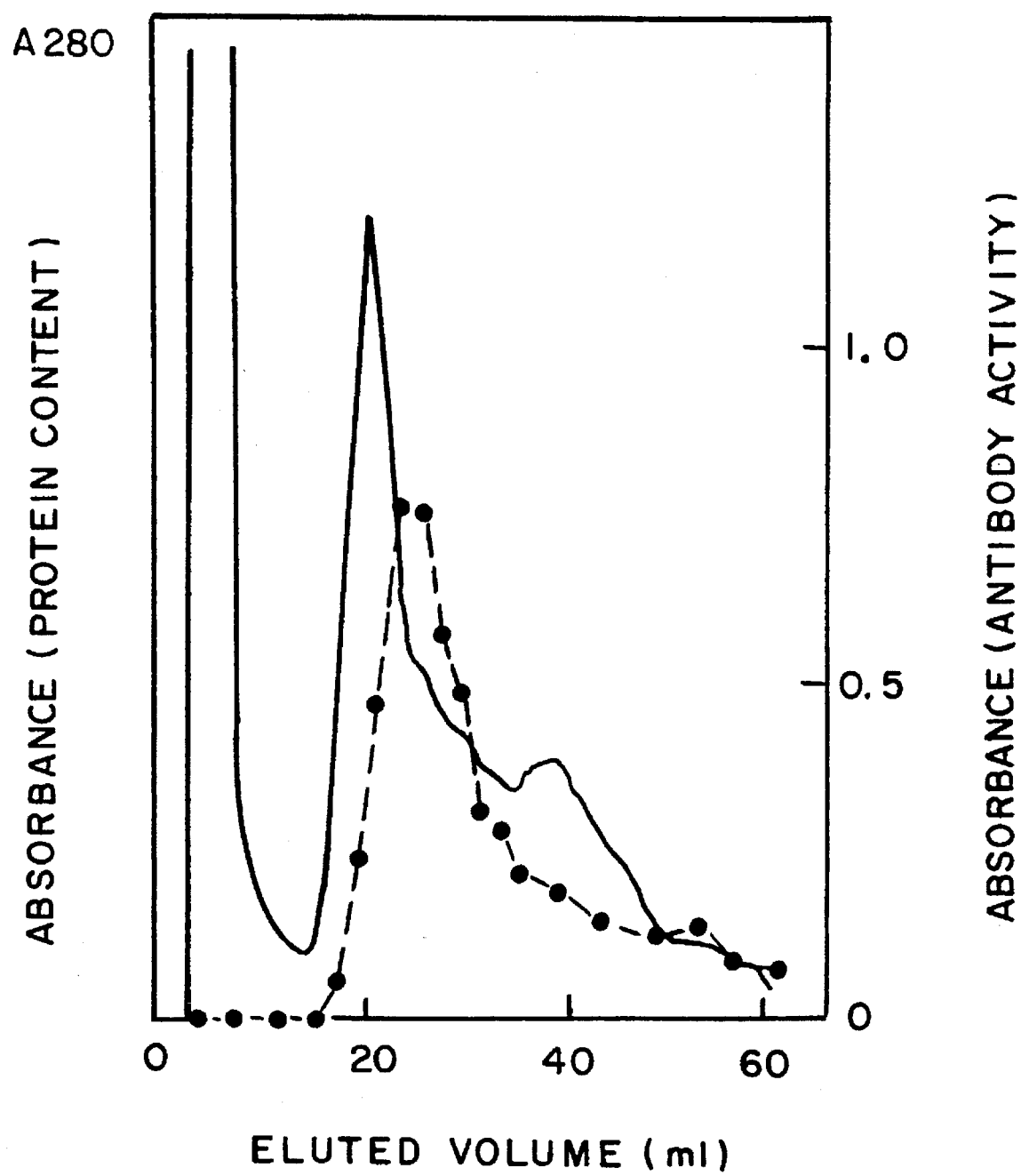
FIG. 3 is a graph showing the results of purified anti-UK-anti-activated platelet bispecific MoAb UP3-175 described in Example 2, namely the results obtained by recovering an IgG fraction from ascites containing antibody UP3-175 by salt precipitation, further purifying the fraction with a UK-bound column, and then subjecting them to a hydroxyapatite column. The solid line indicates the absorbance (the content of the protein) of the eluate at 280 nm, and the dotted line indicates the bispecific antibody activity measured by the EIA described in Reference Example 5.
Figure 4:
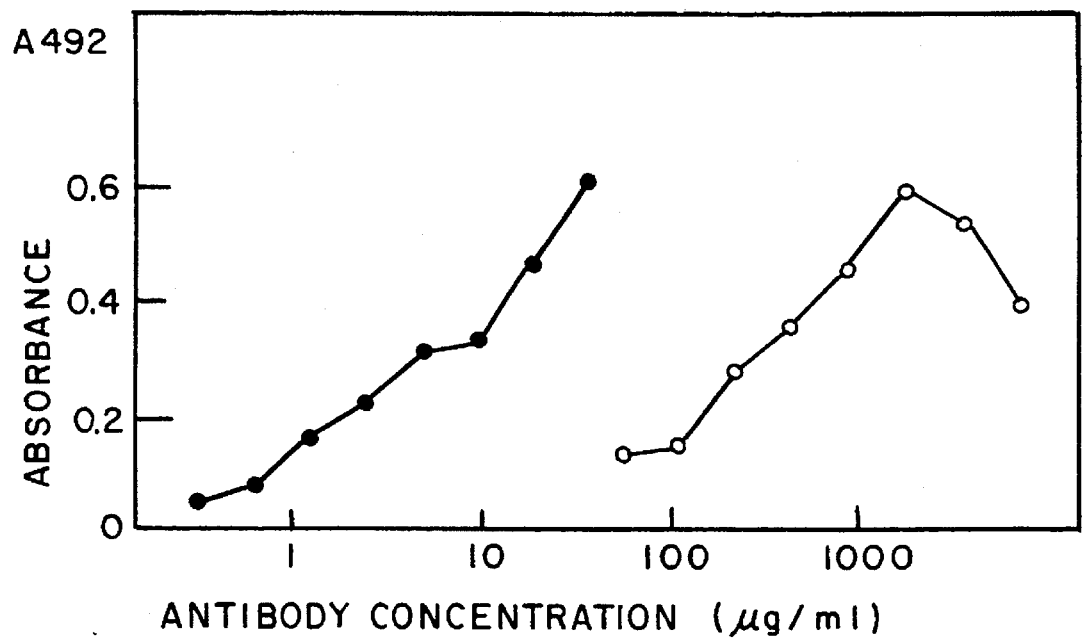
FIG. 4 is a graph showing the bispecific antibody activity measured by the EIA described in Reference Example 5. The graph shows antibody dilution curves of the IgG fraction (o) obtained from ascites containing antibody UP3- 175 by salt precipitation and an acid (pH 2.3)-eluted fraction (•) obtained from the UK-bound column (see Example 2)

The results of purification are as shown in FIGS. 3 and 4. FIG. 3 reveals that a protein fraction containing bispecific MoAb was obtained on the hydroxyapatite. FIG. 4 shows the bispecific antibody activity of the IgG fraction obtained by salt precipitation and the acid (pH 2.3)-eluted fraction obtained from the UK-bound column.

EXAMPLE 3

Preparation of Hybrid Monoclonal Antibody Having Anti-UK-Anti-Activated Platelet Bispecificity (2)

(1) Maleimidation of Anti-UK Antibody

In 2 ml of 5 mM acetate buffer (pH 5.0), 10 mg of anti-UK monoclonal antibody UK1-3 obtained in Reference Example 13 was dissolved, and then 50 μl of a solution of 2-fold moles of N-(ε-maleimidocaproyloxy)succinimide ester in dimethyl formamide was added thereto, followed by reaction at 30° C. for 20 minutes. The reaction mixture was subjected to a Sephadex G-25 (Pharmacia) column equilibrated with 0.1M phosphate buffer (PB, pH 6.5) to remove the binding reagent.

(2) Sulfhydrylation of Anti-Activated Platelet Antibody

In 2 ml of 0.05M PBS (pH 7.3), 10 mg of anti-activated platelet monoclonal antibody 2T60 was dissolved, and then 50 μl of a solution of 2-fold moles of SPDP in methanol was added thereto. After reaction at 30° C. for 30 minutes, 50 μl of a 0.1M aqueous solution of DTT was added thereto, followed by reduction. Then, the resulting product was subjected to the Sephadex G-25 column described in (1) to remove the excess binding agent.

(3) Preparation of Bispecific Antibody

To 8 mg of the maleimidated anti-UK antibody obtained in (1), 8 mg of the sulfhydrylated anti-activated platelet antibody prepared in (2) was slowly added with stirring under ice cooling, followed by reaction overnight. The reaction mixture was subjected to a Sephacryl S-200 (Pharmacia) column to remove unreacted antibodies from chemically bound bispecific antibodies. As a result, about 12 mg of anti-UK-anti-activated platelet bispecific hybrid monoclonal antibody was obtained.

EXAMPLE 4

Preparation of Hybrid Monoclonal Antibody Having Anti-TPA-Anti-Activated Platelet Bispecificity (1) Maleimidation of Anti-TPA Antibody 10 mg of anti-TPA monoclonal antibody TPA2-14 obtained in Reference Example 9-(4) was treated by a method similar to that of Example 3-(1) to obtain about 8 mg of maleimidated antibody TPA2-14.

(2) Preparation of Bispecific Antibody

To 8 mg of the maleimidated antibody obtained in (1), 8 mg of the sulfhydrylated anti-activated platelet antibody prepared in Example 3-(2) was added. According to a method similar to that of Example 3-(3), about 12 mg of anti-TPA-anti-activated platelet bispecific hybrid monoclonal antibody was obtained.

EXAMPLE 5

Preparation of Hybrid Monoclonal Antibody Having Anti-UK-Anti-Activated Platelet Bispecificity (3)

(1) Selection of HAT-Sensitive Strain

Anti-activated platelet specific MoAb-producing hybridoma 2T60 obtained in Example 1 was cultivated in 5 μM 8-AZG-added medium and subcultured for several weeks, increasing the 8-AZG concentration to 100 μM stepwise in turn. The strain having the highest anti-activated platelet MoAb producing activity was selected from the resulting 8-AZG-resistant, HAT-sensitive strains, and subjected to cell fusion.

(2) Cell Fusion

The anti-UK MoAb-producing spleen cells obtained in Reference Example 11-(2) were mixed with HAT-sensitive anti-activated platelet MoAb-producing hybridoma 2T60 in a ratio of 1:5, and cell fusion was conducted by the method described in Reference Example 9-(2), using PEG 6000.

(3) Selection and Cloning of Trioma

After completion of the fusion, the cell mixture was suspended in HAT medium, and selectively cultivated in HAT medium according to the method described in Reference Example 9-(2) to prepare desired trioma cells. A culture supernatant of these trioma cells were subjected to the EIA described in Reference Example 3 to select wells exhibiting positive anti-UK antibody activity. Further, the anti-activated platelet-anti-UK hybrid antibody activity was measured by the EIA described in Reference Example 5. For wells showing high bispecific antibody activity, cloning was performed by the limiting dilution method. As a result, mouse hybrid hybridoma UP4-33 was obtained.

(4) Purification of Hybrid Antibody

Mouse hybrid hybridoma UP4-33 was inoculated to form ascites fluid according to the method described in Example 2-(3). Further, the resulting ascites fluid was purified by using a hydroxyapatite column to obtain mouse anti-UK anti-activated platelet bispecific MoAb UP4-33.

EXAMPLE 6

Enhancement of Fibrinolysis Activity by Hybrid Monoclonal Antibody Having Anti-UK-Anti-Activated Platelet Bispecificity (1)

A platelet-containing plasma clot lysis assay was carried out according to the method known in the art (D. Collen et al., *Thromb. Haemostasis* 45, 225 (1981)). Namely, a bispecific MoAb was added at various concentrations to a definite amount of UK (final concentration: 25 ng/ml), and reacted at room temperature for 20 minutes. Platelet-containing human plasma was added to the resulting UK-MoAb mixture, and then human thrombin was added thereto to a final concentration of 1.0 unit/ml to coagulate the plasma. After 60 minutes, phenylmethylsulfonyl fluoride was added thereto to a final concentration of 1 mM to terminate the UK activity, followed by centrifugation at 16,000 rpm for 5 minutes. The content of FDPs (fibrinogen degradation products) in the supernatant was assayed by a commercial EIA kit (FUJIREBIO), and the UK activity enhancing capability of the bispecific MoAb was determined.

Figure 5:
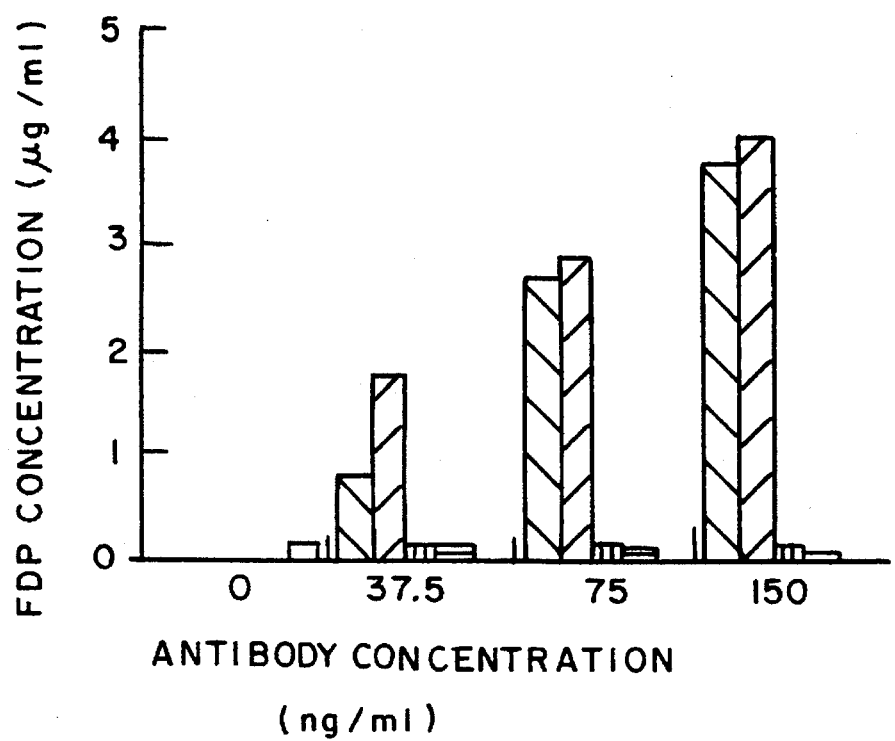
FIG. 5 is a graph showing the content of fibrinogen degradation products (hereinafter occasionally referred to FDPs) assayed by an FDP-EIA kit described in Example 6. Both monospecific antibodies (▥: 2T60 and ▤: UK1-3) do not exert influence on UK activity, but both bispecific antibodies (▨: UP4-33 and ▧: the chemically bound antibody) increase UK activity (□: a control (UK alone)) in proportion to their concentration.

The results are as shown in FIG. 5. For both the chemically bound bispecific antibody described in Example 3 and bispecific MoAb UP4-33 described in Example 5, the fibrinolysis activity was significantly enhanced in proportion to their concentration. In contrast, anti-UK MoAb UK1-3 described in Reference Example 11 and anti-activated platelet MoAb 2T60, the parent strains of the above bispecific antibodies, were both not enhanced in UK activity.

EXAMPLE 7

Enhancement of Fibrinolysis Activity by Hybrid Monoclonal Antibody Having Anti-UK-Anti-Activated Platelet Bispecificity (2)

A platelet-containing plasma clot lysis assay was carried out according to the method described in Example 6. The plasma was coagulated with human thrombin, and then phenylmethylsulfonyl fluoride was added thereto after the elapse of various periods of time to terminate the UK activity. The content of released FDPs was assayed similarly to the method described in Example 6.

Figure 6:
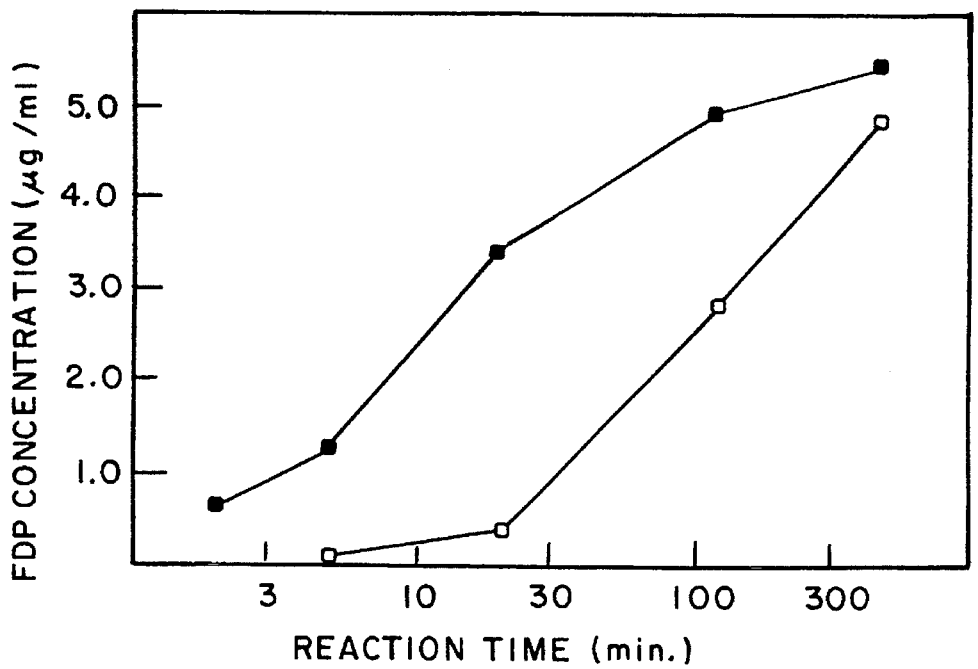
FIG. 6 is a graph showing the content of FDPs assayed by the FDP-EIA kit described in Example 6. The graph shows plasma clot lysis curves of UK alone (□) and the UK/chemically bound bispecific antibody complex (■).

The results are as shown in FIG. 6. Based upon the result, it is clear that plasma clots dissolved rapidly compared to the case of UK alone, when the chemically bound bispecific antibody described in Example 3 coexisted with UK.

The bispecific hybrid MoAbs of the present invention do not substantially bind to the resting platelets and do specifically bind to the activated platelets alone. They also bind to the substances having thrombolytic activity without impairing their fibrinolysis activity.

Accordingly, 1:1 immune complexes of the bispecific hybrid MoAbs and the substances having thrombolytic activity can be easily prepared. It is possible to dissolve and remove thrombi selectively and efficiently by using both in combination.

Furthermore, when the anti-fibrin-anti-thrombolytic active substance bispecific MoAbs are used in combination with the thrombolytic active substances, more efficient, rapid thrombolysis becomes possible.

EXAMPLE 8

Enhancement of Fibrinolysis Activity by Hybrid Monoclonal Antibody Having Anti-UK-Anti-Activated Platelet Bispecificity (3)

The anti-UK-anti-activated platelet bispecific MoAbs described in Example 5 were added at various concentrations to a definite amount of UK (final concentration: 25 ng/ml), and reacted at room temperature for 20 minutes. A platelet-containing plasma clot lysis assay was carried out according to the method of Example 6, by adding platelet-containing human plasma or human plasma without platelet to the resulting UK-MoAb mixture, and then adding human thrombin thereto to coagulate the plasma. The content of FDPs in the supernatant was assayed by a commercial EIA kit, and the UK activity enhancing capability of the bispecific MoAb was determined.

Figure 7:
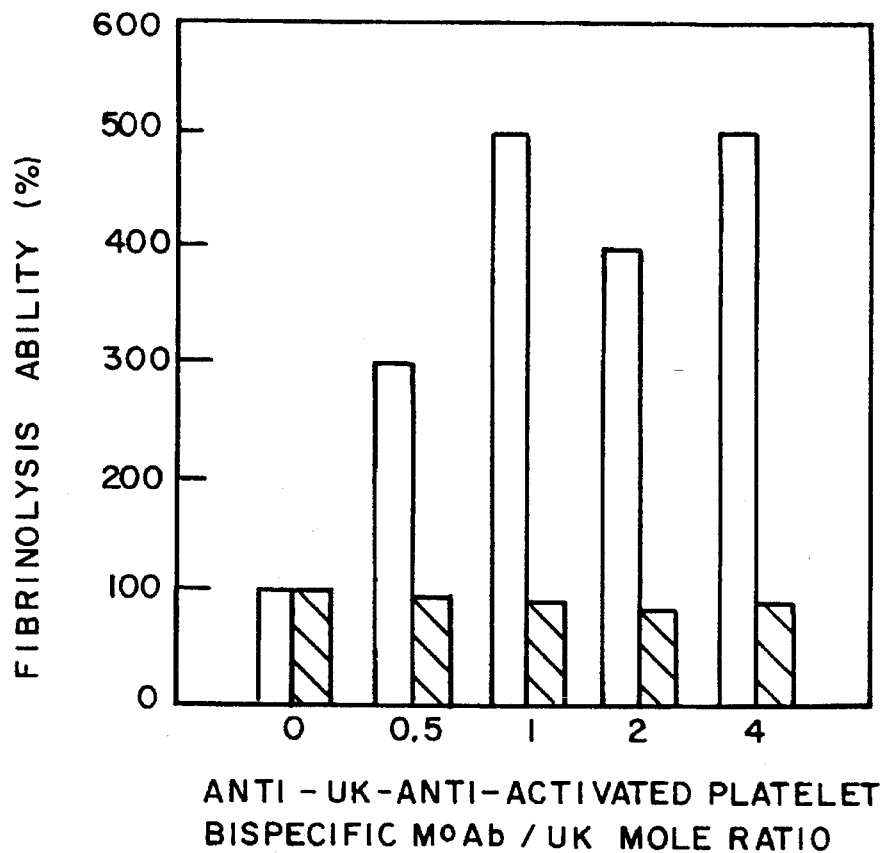
FIG. 7 is a graph showing the result of a clot lysis assay described in Example 8 for platelet containing human plasma (▭) and human plasma without platelet (▨). The vertical axis indicates the content of FDPs when using bispecific MoAb UP4-33/UK complex, as the FDP content is 100(%) when using UK alone (See Example 8).

The results are as shown in FIG. 7. For a plasma clot without platelet, MoAb UP4-33 did not enhance the UK fibrinolysis activity. In contrast, for a platelet-containing plasma clot, bispecific MoAb UP4-33 enhanced significantly the UK fibrinolysis activity in proportion to its concentration.

EXAMPLE 9

Enhancement of Fibrinolysis Activity by Hybrid Monoclonal Antibody Having Anti-UK-Anti-Activated Platelet Bispecificity (4)

To 50 ng/ml UK solution, was added an equal amount of bispecific MoAb of 150 ng/ml [(1) anti-UK-anti acactivated platelet bispecific MoAb UP 4-33 described in Example 5; (2) anti-UK-anti fibrin bispecific MoAb FU 1-74 described in Reference Example 18; or (3) 1:1 mixture of bispecific MoAb UP4-33 and FU1-74]. After the reaction, a clot lysis assay was carried out according to the method of Example 6 by adding platelet-containing plasma to the mixture.

Figure 8:
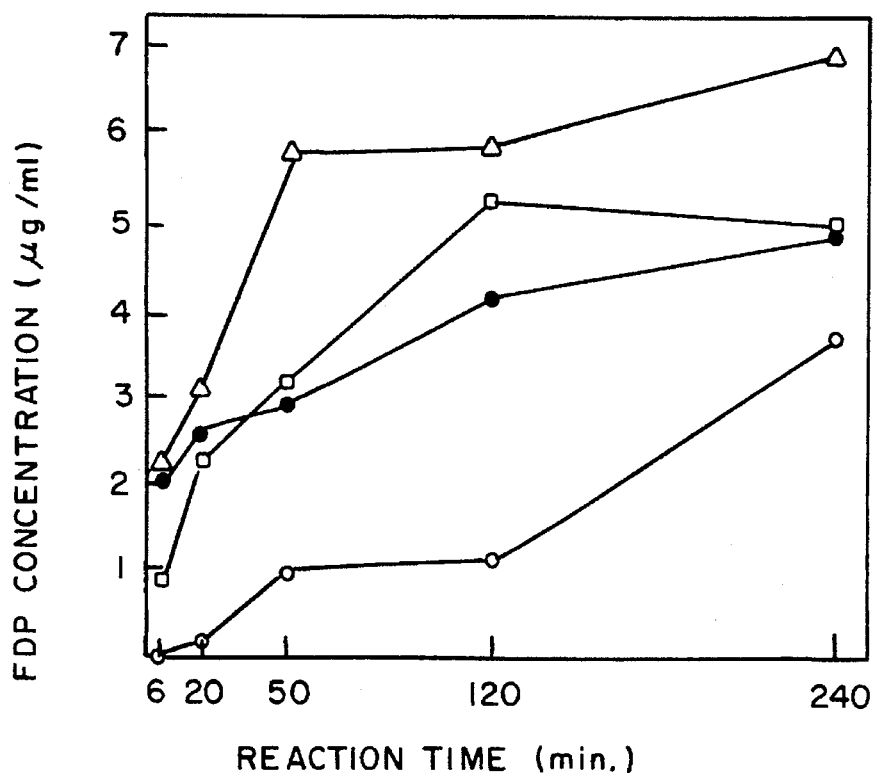
FIG. 8 is a graph showing the content of FDPs assayed by FDP-EIA described in Example 9, wherein the content of FDP in the supernatant was assayed while centrifugation of the reaction mixture was carried out at the indicated times. The graph shows plasma clot lysis curves of UK alone (o), anti-UK-anti-activated platelet bispecific MoAb UP4-33 (□), anti-UK-anti-fibrin bispecific MoAb FU1-74 (•), and 1:1 mixture of bispecific MoAbs FU1-74 and UP4-33 (Δ).

The results are shown in FIG. 8. Both the bispecific MoAb FU1-74 described in Reference Example 18 and the bispecific MoAb UP4-33 described in Example 5 enhanced the UK fibrinolysis activity. Further, the 1:1 mixture of the bispecific antibodies enhanced synergitically the UK fibrinolysis speed and amount compared with when using each alone.

EXAMPLE 10

Enhancement of Fibrinolysis Activity by Hybrid Monoclonal Antibody Having Anti-UK-Anti-Activated Platelet Bispecificity (5)

(1) Preparation of $^{125}$I-Labeled Plasma Clot

Commercial $^{125}$I-labeled human fibrinogen (10 μg/10 μl; sold by Muromachi Kagaku Kogyo) was added to 600 μl of platelet-containing human plasma, and then bovine thrombin (1 unit/100 μl) was added thereto, followed by rapid stirring. The resulting mixture was sucked up into a catheter treated with 10% Tween 80, and allowed to stand at room temperature for 1 minute, followed by further incubation at 37° C. for 30 minutes. The resulting plasma clots were extruded on a plate (Schale) on which physiological saline is placed, and cut at intervals of 1 cm with a knife. The radiation activity of each section was measured by a γ-counter.

(2) Model Experiment of Hamster Pulmonary Emboli

Pentobarbital (6 mg/0.3 ml) was given intraperitoneally to each hamster (having a body weight of 80 to 100 g), followed by insertion of a catheter for blood collection into the femoral vein. Then, the $^{125}$I-labeled plasma clots prepared in (1) were sucked up into a catheter and injected into the jugular vein, followed by insertion of a catheter for sample administration. NaI (0.2 mg/0.1 ml) and heparin (100 units/0.1 ml) were given through the jugular vein, and then 350 μl of prourokinase (ProUK) or the immune complex prepared by adding 2-fold moles of the bispecific MoAb described in Example 5 to ProUK was given. After standing at room temperature for 90 minutes, the blood (1 ml) was collected, and the breast was opened to remove the right lung, the left lung and the heart. The radioactivity of each organ was measured by a γ-counter. The lysis rate of the plasma clots was determined from a ratio of the amount of residual radioactivity in the three organs to the total amount of the given radioactivity.

The results are as shown in Table 1. The lysis activity of ProUK was enhanced twice or more by addition of bispecific MoAb UP4-33.

TABLE 1

| Sample (mg/kg) | | Lysis rate of plasma clots (%) |
|---|---|---|
| ProUK | Bispecific MoAb | |
| Control | | 10 ± 7 |
| 0.5 | — | 29 ± 1 |
| 1.0 | — | 48 ± 8 |
| 2.0 | — | 67 ± 14 |
| 4.0 | — | 73 ± 11 |
| 0.5 | 3.0 | 35 ± 6 |
| 1.0 | 6.0 | 68 ± 10 |
| 2.0 | 12.0 | 86 ± 4 |

EXAMPLE 11

Effect of Hybrid Monoclonal Antibody Having Anti-UK-Anti-Activated Platelet Bispecificity on ADP-Induced Platelet Aggregation 200 μl of platelet-containing human plasma was added to a cuvet of a 6-channel aggregation meter (Niko Bioscience; NKK Hematracer I-model T-634), and stirred at 37° C. Furthermore, 12.5 μl of a plasminogen solution (final concentration: 0.5 μg/ml) and 25 μl of a UK/bispecific MoAb immune complex solution were added thereto at the same time. After 1 minute, 20 μl of an ADP solution (final concentration: 1.2 μM) was added thereto to observe an aggregation curve.

The UK/bispecific MoAb immune complex was prepared by adding the equimolar MoAb (final concentration: 16.6 μg/ml) to UK (final concentration: 5.6 μg/ml), and incubating the mixture at room temperature for 30 minutes. As a control, a mixed solution prepared by adding the equimolar normal mouse IgG to UK was used.

Figure 9:
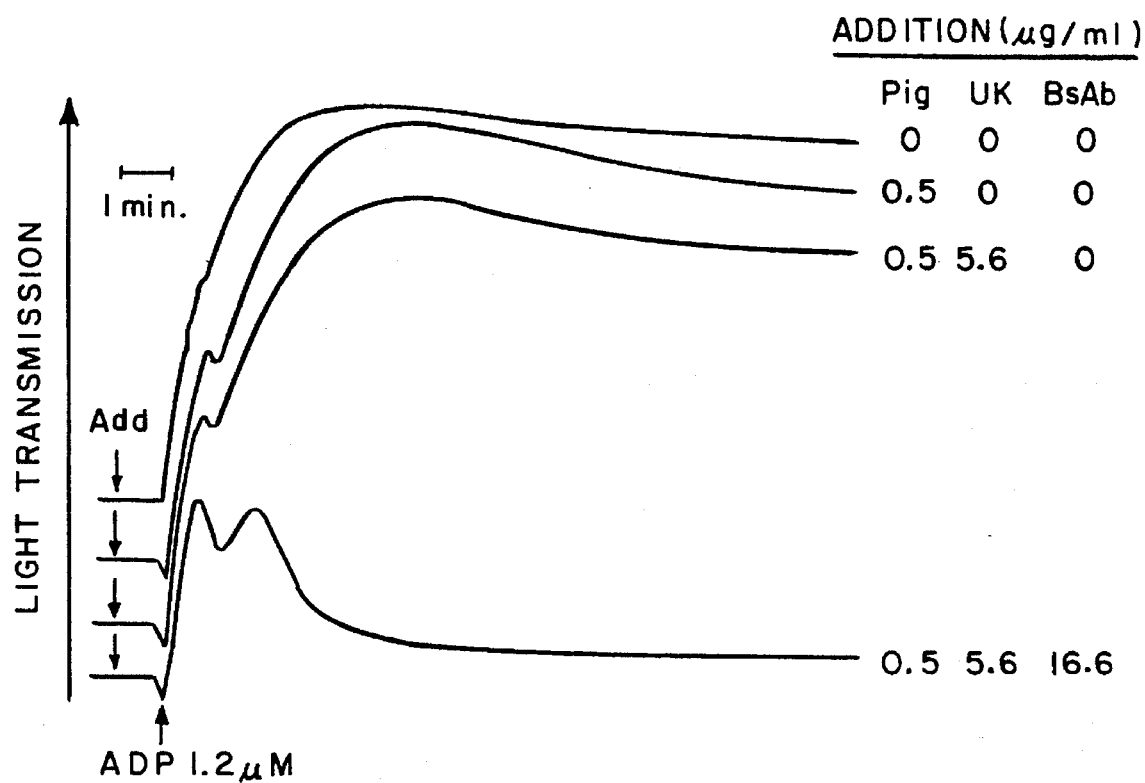
FIG. 9 is a graph showing the ADP coagulation curve of human platelets described in Example 11.

The results obtained are as shown in FIG. 9. For the UK/normal mouse IgG mixed solution, ADP-induced aggregation was scarcely affected. However, the UK/bispecific MoAb immune complex significantly dissociated the secondary aggregation wave of ADP-induced human platelet aggregation.

The following references, which are referred to for their disclosures at various points in this application, are incorporated herein by reference.

European Cooperative Study Group for Recombinant Tissue-Type Plasminogen Activator: The Lancet, Vol.1, 842 (1985)

Science 229, 765 (1985)

Proc. Natl. Acad. Sci. USA 84, 7659 (1987)

Japanese Patent Unexamined Publication No. 2-500321/1990

European Patent Unexamined Publication No. 363712/1990

Proc. Natl. Acad. Sci. USA 86, 1036 (1989)

Thromb. Haemostasis 62, 3 (1989)

Thromb. Haemostasis 62, 250 (1989)

J. Clin. Invest. 78, 130 (1986)

Science 243, 51 (1989)

J. Immunol. 139, 2367 (1987)

Organic Synthetic Chemistry 42, 283 (1984)

Proteins, Nucleic Acids, Enzymes 33, 217 (1988)

Mol. Cell. Biol., 5, 410 (1985)

J. Immunol. Methods 96, 265 (1987)

Proc. Natl. Acad. Sci. USA 85, 4852 (1988)

Nature 256, 495 (1975)

Thromb. Haemostasis 45, 225 (1981)

What is claimed is:

1. A bispecific hybrid monoclonal antibody having specificity for both an activated platelet and a protease.

2. The bispecific antibody according to claim 1, in which said activated platelet is a human platelet activated with thrombin.

3. The bispecific antibody according to claim 1, in which said protease is urokinase.

4. The bispecific antibody according to claim 1, in which said protease is prourokinase.

5. The bispecific antibody according to claim 1, in which said protease is tissue plasminogen activator.

6. A bispecific monoclonal antibody produced by the mouse hybrid-hybridoma deposited as FERM BP-2845.

7. A bispecific monoclonal antibody produced by the mouse hybrid-hybridoma deposited as FERM BP-3018.

8. A thrombolytic agent comprising the bispecific monoclonal antibody claim 7 and a therapeutically effective amount of a protease having thrombolytic activity.

9. The thrombolytic agent according to claim 8, in which said protease is prourokinase.

10. The thrombolytic agent according to claim 8, in which said protease is tissue plasminogen activator.

11. The thrombolytic agent according to claim 8, in which said protease is urokinase.

12. A method for lysis of a thrombus in a mammal, which comprises administering to said mammal suffering from a thrombus, an effective amount of the bispecific monoclonal antibody of claim 7 and a therapeutically effective amount of a protease having thrombolytic activity.

13. The method of claim 12, wherein the administration step comprises administering to said mammal a second bispecific hybrid monoclonal antibody, FERM BP-2344, having specificities for both fibrin and urokinase and having thrombolytic activity.

* * * * *